(12) United States Patent
Nakamura

(10) Patent No.: US 7,485,115 B2
(45) Date of Patent: Feb. 3, 2009

(54) REMOTE OPERATION SUPPORT SYSTEM AND METHOD

(75) Inventor: Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 771 days.

(21) Appl. No.: 10/714,766

(22) Filed: Nov. 17, 2003

(65) Prior Publication Data

US 2004/0230094 A1     Nov. 18, 2004

(30) Foreign Application Priority Data

Nov. 20, 2002  (JP) ............................ 2002-336998
Nov. 11, 2003  (JP) ............................ 2003-381773

(51) Int. Cl.
*A61B 17/00* (2006.01)

(52) U.S. Cl. ........................... 606/1; 600/102; 600/118; 348/211.1; 348/211.2; 348/211.3; 348/211.4; 348/211.99; 348/14.09; 434/262

(58) Field of Classification Search ..................... 606/1; 348/211.99–211.4; 434/262
See application file for complete search history.

(56) References Cited

U.S. PATENT DOCUMENTS

| | | | |
|---|---|---|---|
| 6,602,185 B1 * | 8/2003 | Uchikubo | 600/118 |
| 6,659,939 B2 * | 12/2003 | Moll et al. | 600/102 |
| 6,697,764 B2 * | 2/2004 | Corby et al. | 702/184 |

2002/0147384 A1  10/2002  Uchikubo

FOREIGN PATENT DOCUMENTS

JP       2002-306509       10/2002

* cited by examiner

*Primary Examiner*—Linda C Dvorak
*Assistant Examiner*—Matthew J. Kasztejna
(74) *Attorney, Agent, or Firm*—Scully, Scott, Murphy & Presser, P.C.

(57) ABSTRACT

According to the present invention, a remote operation support system includes a first control system arranged in an operating room, a second control system arranged in a primary support room, and a third control system arranged in at least one secondary support room, the first to third control systems being connected to each other through communication lines. The first control system has an imaging device for obtaining an image signal of a patient under operation, a first transmission/reception device for transmitting the image signal supplied from the imaging device to the second control system, simultaneously transmitting patient information regarding the patient under operation to the third control system, and receiving support information from the second control system, and a reproduction device for displaying the image signal and reproducing the support information. On the basis of secondary support information sent from the third control system and the image signal sent from the first control system, the second control system generates primary support information to support an operator in the operating room upon operating, and then transmits the generated information to the first control system.

21 Claims, 6 Drawing Sheets

REMOTE OPERATION SUPPORT SYSTEM AND METHOD

This application claims benefit of Japanese Application Nos. 2002-336998 filed on Nov. 20, 2002, and 2003-381773 filed on Nov. 11, 2003 and the contents of which are incorporated by this reference.

BACKGROUND OF THE INVENTION

1. Field of the Invention

The present invention relates to a remote operation support system and method capable of properly supporting an operator in remote operation support.

2. Description of Related Art

Endoscopes have been generally used in the field of medical treatment. Recently, endoscopes equipped with a television camera and electronic endoscopes have been widespread. Each television-camera-equipped endoscope is designed in such a manner that imaging means is provided for an eyepiece of an optical endoscope. Each electronic endoscope has imaging means embedded at the distal end. Endoscopic apparatuses each utilize such an endoscope. In the apparatus, since an endoscopic image captured by the endoscope is displayed on a monitor, an operator can observe and treat a patient while viewing the image.

The endoscopic apparatus connects to a light source supplying an illumination beam to the endoscope, a video processor functioning as a camera control unit with an image signal processing circuit for displaying an endoscopic image, and a television monitor in which the endoscopic image is displayed. Further, other peripheral devices such as a gas insufflator and a high-frequency cauterizer are provided for the endoscopic apparatus, thus constructing an endoscopic system capable of performing treatment or an operation while observing with the endoscope. This system is in practical use.

In the above-mentioned endoscopic system, generally, those peripheral devices are connected to a system controller, resulting in a centralized control.

Usually, an operator operates on a patient in an operating room. For example, in some cases, the operator in the operating room has to perform a certain operation which he or she has performed only few times, namely, the operator may be a poor experienced operator with respect to that operation. The following system would be applied to the above case: A terminal disposed near the operator is connected to a terminal of another operator in a remote location (hereinbelow, referred to as a remote supporting operator) through a communication line, the remote supporting operator being familiar to that operation, namely, having rich experience in the operation. During the operation, the remote supporting operator can give directions to the operator with respect to an affected area to be removed. Through the use of the above-mentioned system, the operator in the operating room can perform the operation while receiving remote support. Thus, the operator can properly perform the operation on the patient in the operating room.

In an operation with the endoscopic observation mentioned above, even if an operator in an operating room is an inexperienced doctor, he or she receives directions from an experienced doctor serving as a remote supporting operator while the remote supporting operator is observing endoscopic images displayed on a monitor, so that the doctor in the operating room can perform the operation with reliability. In this instance, an endoscopic image of an operating field to be displayed on the monitor is important. If an endoscopic image displayed is different from that of an operating field which the experienced doctor desires to view, the doctor verbally or directly directs the operator in the operating room to capture an endoscopic image including the desired operating field. Thus, the operator can smoothly perform the operation in collaboration with the remote supporting operator.

As mentioned above, according to the foregoing remote operation support system, if an experienced doctor, serving as a supporting operator giving directions, lives in a remove location, a terminal disposed in a hospital where the doctor works is connected to a terminal disposed in an operating room where another doctor in charge of an operation exists through a public line so that the doctor properly operates on a patient in the operating room while receiving directions from the doctor in the remote location during the operation. As a related art of the above system, Japanese Unexamined Patent Application Publication No. 2002-306509 (Japanese Patent Application No. 2001-111749), to the same assignee as this application, proposes a remote operation support system.

This proposal intends to achieve an object to provide a remote operation support system capable of integrally displaying an endoscopically-observed image and instruction information, transmitted from a remote location, on one monitor without deteriorating an operation in an operating room.

SUMMARY OF THE INVENTION

According to the present invention, a remote operation support system includes a first control system disposed in an operating room, a second control system disposed in a primary support room, and a third control system disposed in at least one secondary support room, the first to third control systems being connected to each other through communication lines. The first control system includes: an imaging device for imaging a portion to be treated of a patient under operation to obtain an image signal; a first transmission/reception device for transmitting the image signal supplied from the imaging device to the second control system, simultaneously transmitting patient information regarding the patient under operation to the third control system, and receiving support information from the second control system; and a reproduction device for displaying the image signal and reproducing the support information. The third control system includes: a patient-information processing device for processing the patient information transmitted from the first control system to obtain the result of the processing; and a second transmission/reception device for receiving the patient information from the first transmission/reception device of the first control system, and transmitting information indicating the processing result, obtained by the patient-information processing device, as secondary support information to the second control system. The second control system includes: an integration device for generating primary support information, used to support an operator in the operating room upon operating, on the basis of the secondary support information sent from the third control system and the image signal sent from the first control system; and a third transmission/reception device for receiving the image signal sent from the first control system and the secondary support information sent from the third control system, and transmitting the primary support information generated through the integration device to the first control system.

DETAILED DESCRIPTION OF THE PREFERRED EMBODIMENTS

An embodiment of the present invention will now be described hereinbelow with reference to the drawings.

Figure 1:
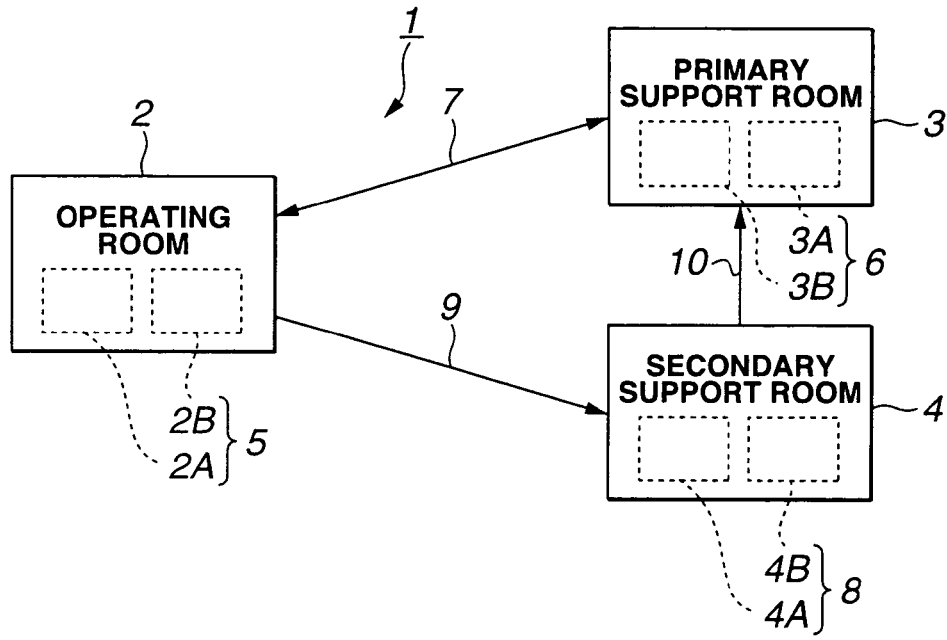
FIG. 1 is a block diagram schematically showing the whole structure of a remote operation support system to explain the remote operation support system and method according to an embodiment of the present invention.
Figure 2:
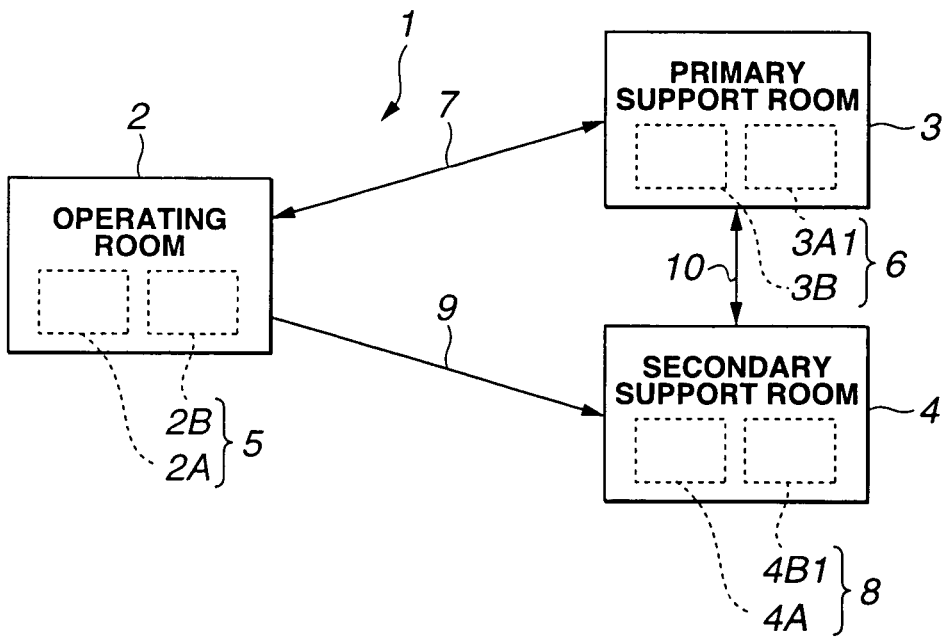
FIG. 2 is a block diagram showing a modification of the remote operation support system according to the above embodiment of the present invention.
Figure 3:
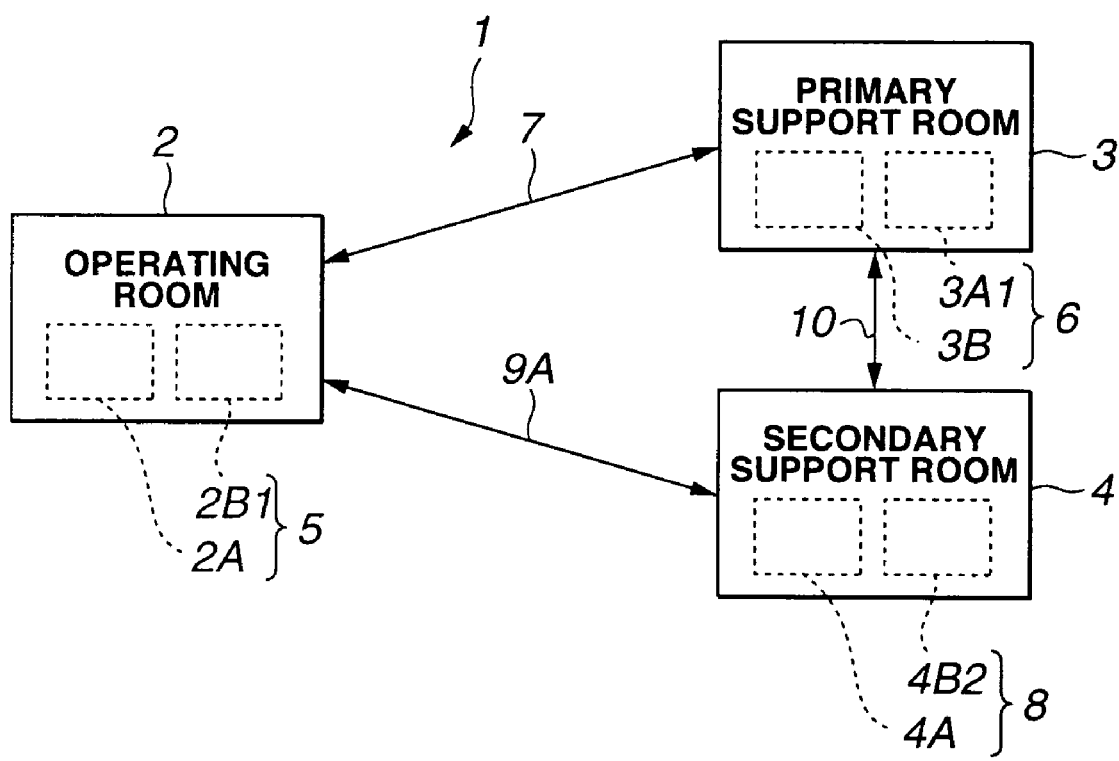
FIG. 3 is a block diagram showing another modification of the remote operation support system according to the embodiment of the present invention.
Figure 4:
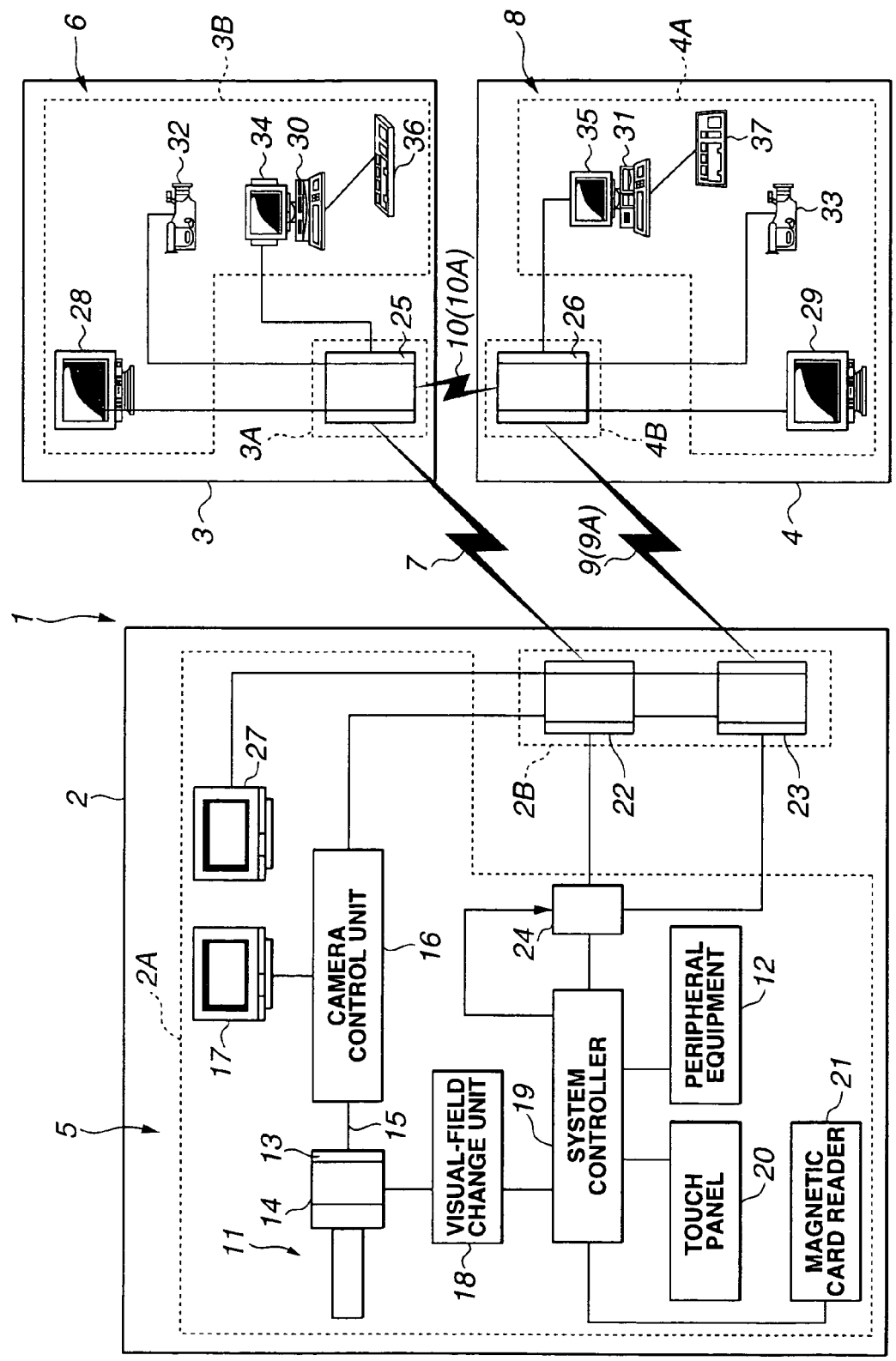
FIG. 4 is a block diagram showing a concrete example of the whole structure of the remote operation support system according to the present embodiment.
Figure 5:
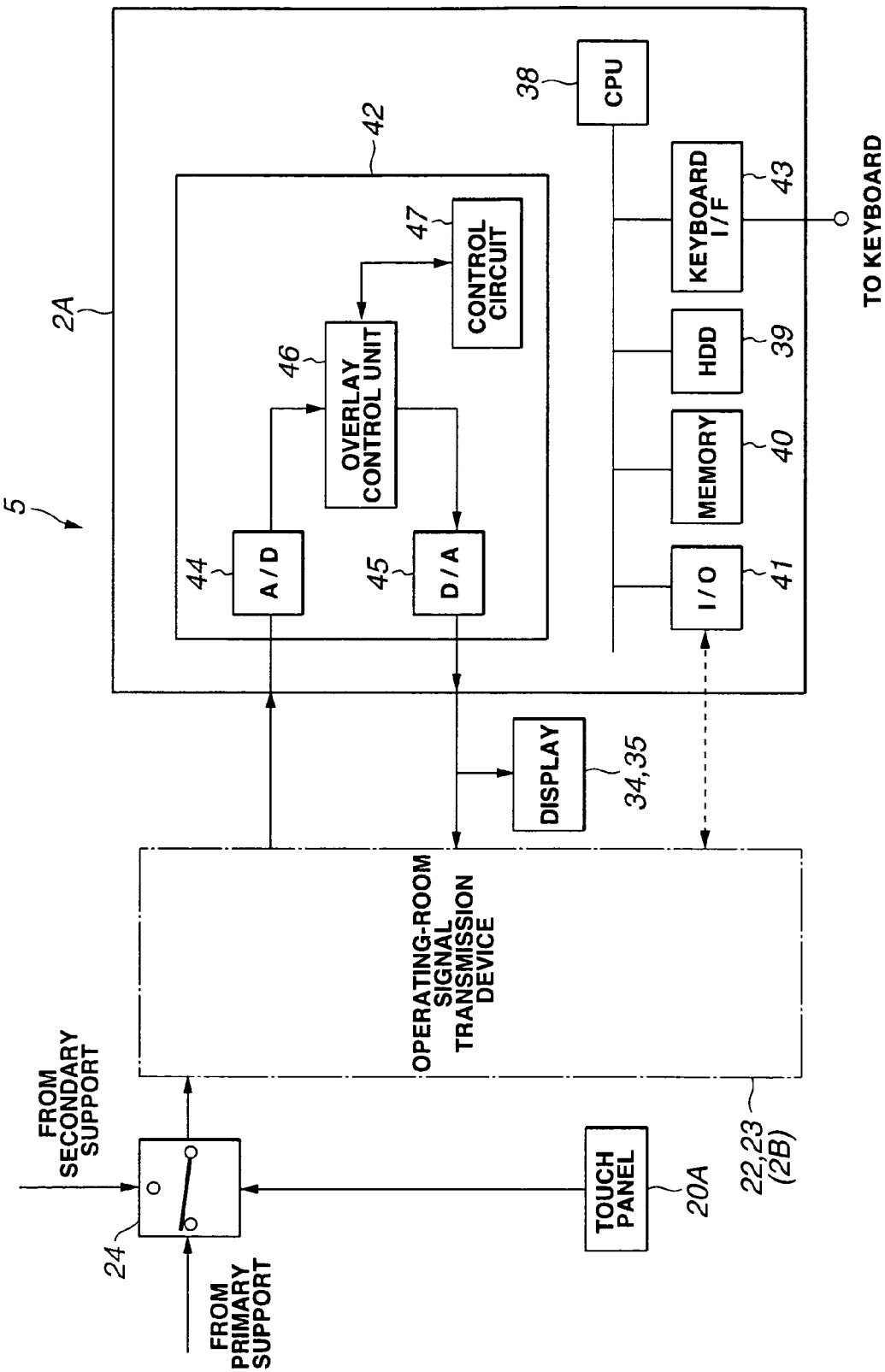
FIG. 5 is a block diagram showing the whole structure of an endoscopic system in an operating room.
Figure 6:
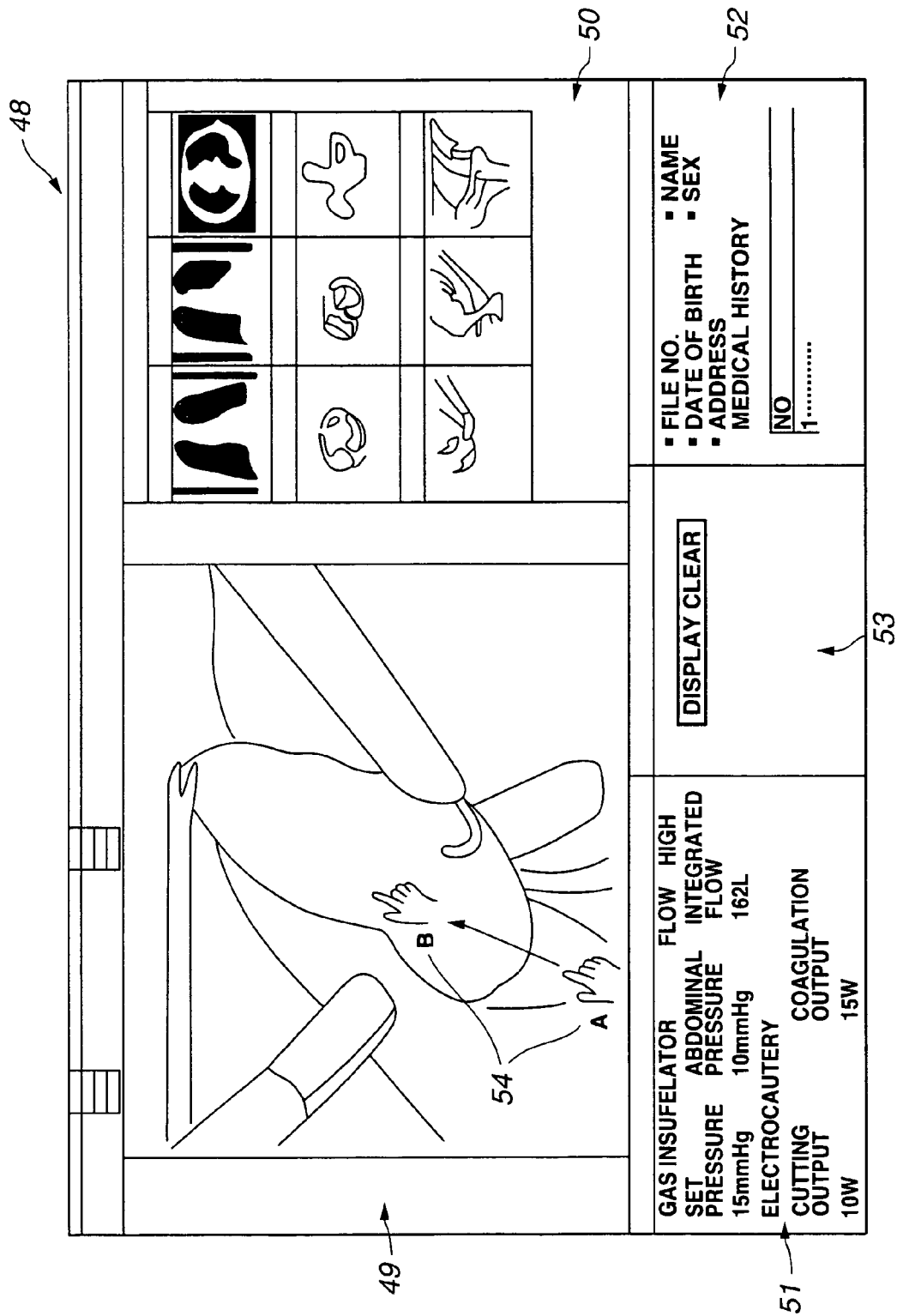
FIG. 6 is a diagram showing a display example to explain the operation of the remote operation support system.
Figure 7:
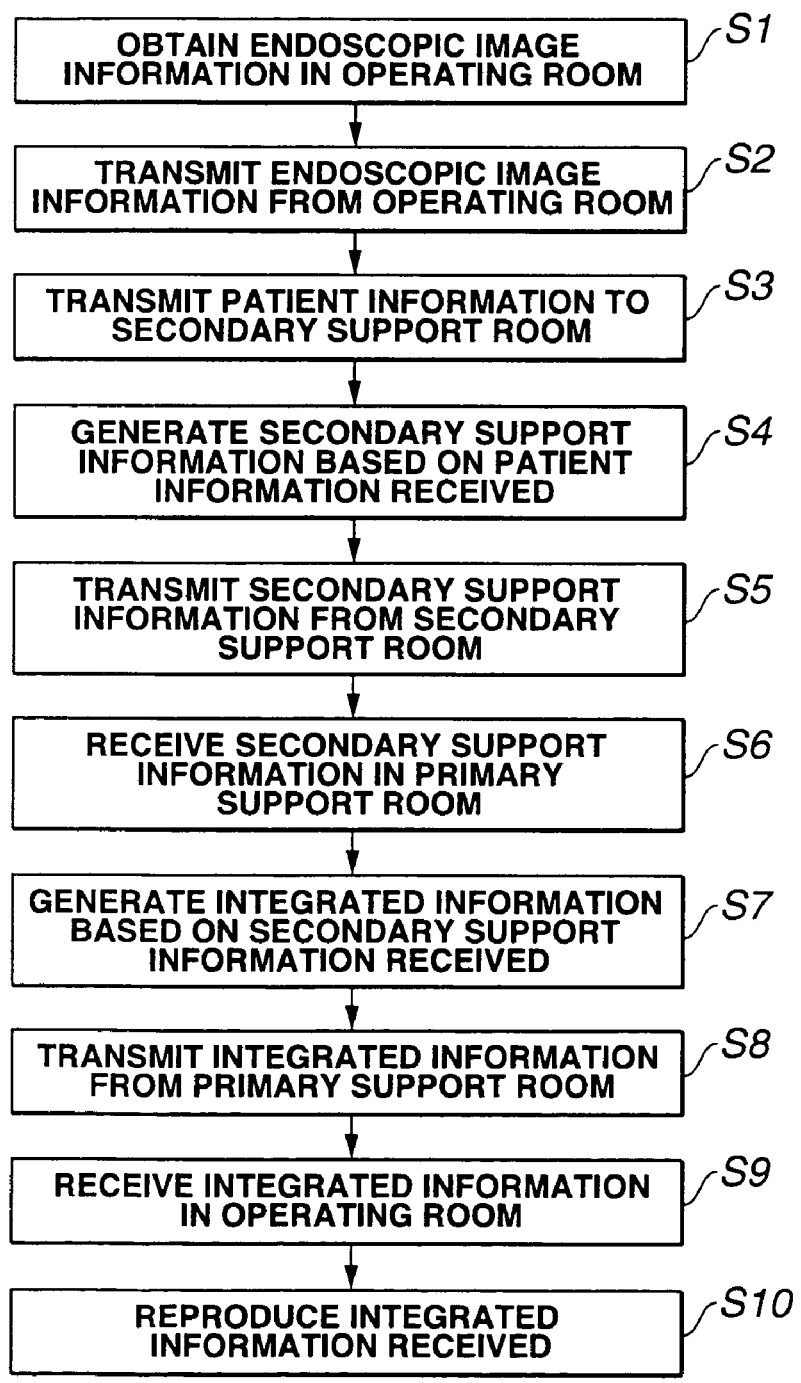
FIG. 7 is a flowchart showing an example of a procedure of the remote operation support method according to the present embodiment.

FIGS. 1 to 6 are diagrams explaining a remote operation support system and method according to the present embodiment of the present invention. FIG. 1 is a block diagram schematically showing the whole structure of the remote operation support system to explain the remote operation support system and method according to the present embodiment of the present invention. FIGS. 2 and 3 are block diagrams showing modifications of the remote operation support system. FIG. 4 is a block diagram showing a concrete example of the whole structure of the remote operation support system according to the present embodiment. FIG. 5 is a block diagram showing the whole structure of an endoscopic system in an operating room. FIG. 6 is a diagram showing a display example to explain the operation of the remote operation support system. FIG. 7 is a flowchart showing an example of a procedure of the remote operation support method according to the present embodiment.

Referring to FIG. 1, according to the present embodiment, a remote operation support system 1 comprises: an endoscopic system 5 in an operating room 2, where an operator actually performs an operation; a remote control system 6 in a primary support room 3, where an supporter remotely supports the operator in the operating room 2; and a remote control system 8 in a secondary support room 4, where an examination is performed on the basis of patient information sent from the operating room 2 and the result of the examination is transmitted to the primary support room 3, thus assisting the support given from the primary support room 3.

The endoscopic system 5 in the operating room 2 is connected to the remote control system 6 in the primary support room 3 through a two-way communication line 7. The endoscopic system 5 in the operating room 2 is connected to the remote control system 8 in the secondary support room 4 through a communication line 9 for one-way communication from the operating room 2 to the secondary support room 4.

The remote control system 6 in the primary support room 3 is connected to the remote control system 8 in the secondary support room 4 through a communication line 10 for one-way communication from the secondary support room 4 to the primary support room 3.

Therefore, when obtaining patient information as operation information supplied from the operating room 2, the remote control system 8 in the secondary support room 4 transmits support information items regarding the examination result obtained on the basis of the patient information, to the remote control system 6 in the primary support room 3. The remote control system 6 in the primary support room 3 can select at least one necessary support information item from among the received information items and then transmit the selected support information to the endoscopic system 5 in the operating room 2. Thus, the operating room 2 receives the support information transmitted from only the primary support room 3 and does not receive all of the information items regarding the examination result, which are obtained in the secondary support room 4 and are not selected. Advantageously, the operator is free from a troublesome work such as selection of a necessary information item among received information items.

The structure of the remote operation support system will now be described in more detail. The endoscopic system 5 in the operating room 2 includes an endoscope, reproduction means 2A, and transmission/reception means 2B. The endoscopic system 5 includes a control system whereby the operator in the operating room 2 performs an operation while receiving remote support. The reproduction means 2A includes a reproduction device for reproducing the patient information as operation information and integrated information as support information transmitted from the primary support room 3. The transmission/reception means 2B receives the patient information obtained during the operation, also receives the support information from the primary support room 3, transmits an endoscopically-observed image during the operation to the primary support room 3 in real time, and also transmits the patient information during the operation to the secondary support room 4. Patient information may include image information of, for example, tissue removed or a specimen, patient-specific information such as a blood pressure or brain waves specific to a patient, information indicating whether each device used in the operation is operable, and information such as a voice of an operator in the operating room or video information of the patient. The removed tissue or specimen of the patient is conveyed from the operating room 2 to the secondary support room 4 in order to examine the removed tissue or specimen. In the secondary support room 4, the removed tissue or the like is pathologically examined. The endoscopic system 5 functions as a system for generating patient information during or before the operation, or an endoscopically-observed image to conduct an endoscopic diagnosis.

The reproduction means 2A comprises a monitor serving as, for example, image display means which will be described later, a microphone, and a loudspeaker, the microphone and the loudspeaker serving as audio playback means. The reproduction means 2A reproduces an image or a voice based on the above-mentioned support information using the respective components to support the operator during the operation.

The transmission/reception means 2B transmits an endoscopically-observed image in the operation to the primary support room 3 in, for example, real time, receives support information from the primary support room 3, and supplies the received support information to the reproduction means 2A. Moreover, the transmission/reception means 2B transmits patient information to the secondary support room 4 in order to make an examination based on the patient information. The patient information is obtained during the operation and includes an image of removed tissue or a specimen, or patient-specific information.

In the description of the present embodiment, the transmission/reception means 2B in the operating room 2 transmits patient information obtained during the operation to the secondary support room 4. The embodiment is not limited to this case. Patient information obtained before the operation may be previously transmitted to the secondary support room 4 and an examination may be performed on the basis of the patient information in the secondary support room 4 before or during the operation.

On the other hand, in the secondary support room 4, the remote control system 8 receives patient information from the operating room 2. The remote control system 8 comprises at least transmission/reception means 4B and examination means 4A. The transmission/reception means 4B includes a transmission/reception device for receiving the patient information and transmitting support information (hereinbelow, referred to as secondary support information) to the primary support room 3, the secondary support information being derived from an examination based on the received patient information. The examination means 4A includes a patient-information processing device for processing the received patient information. Specifically, the examination means 4A includes an examination device for conducting an examination on the basis of the received patient information and supplying the result of the examination to the transmission/reception means 4B to transmit the result to the primary support room 3. The remote control system 8 includes a control system for remotely providing secondary support information to the supporter in the primary support room 3.

The patient information received through the transmission/reception means 4B is used for examination through the examination means 4A. Information regarding the examination result is transmitted as secondary support information together with the pathological examination result of the removed tissue or specimen to the primary support room 3 through the transmission/reception means 4B.

The examination means 4A may include an examination device in an organization for pathologic examinations of removed tissue and specimens, the organization including, for example, a pathologic laboratory of a hospital in affiliation. The secondary support information includes a voice, characters, an image, or numeric data indicating the examination result based on the patient information.

Examination means may include a device for reproducing patient information so that the supporter can recognize information regarding the patient in the operating room. In this case, secondary support information may include information such as advice of a supporter in the secondary support room 4 with respect to the operation in the operating room.

Referring to FIG. 1, one secondary support room 4 is arranged. A plurality of secondary support rooms can also be disposed. In this case, the structure of each secondary support room is the same as that of the secondary support room 4. The respective secondary support rooms are connected to the operating room 2 through connection lines similar to the foregoing communication line therebetween.

In the primary support room 3, the remote control system 6 receives the secondary support information from the secondary support room 4. The remote control system 6 comprises transmission/reception means 3A and integration means 3B. The transmission/reception means 3A includes a transmission/reception device for receiving an endoscopically-observed image sent from the operating room 2 and secondary support information sent from the secondary support room 4, and transmitting integrated information as support information to the operating room 2. The integrated information is generated by the integration means 3B, which will be described hereinbelow. The integration means 3B includes an integration device for generating the optimum support information (hereinbelow, referred to as integrated information) for the operator in the operating room 2. Using the integration means 3B, the supporter as an experienced doctor generates the integrated information on the basis of the endoscopically-observed image and the secondary support information received through the transmission/reception means 3A. The remote control system 6 includes a control system for remotely supporting the operator in the operating room 2.

The primary support room 3 is remote from the operating room 2. The experienced doctor is on standby in the primary support room 3, the doctor capable of supporting the operator in the operating room 2 to perform the optimum operation while suggesting a manipulation or making a description. The experienced doctor uses the remote control system 6 to generate the integrated information, including the manipulation or description, on the basis of the endoscopically-observed image and the secondary support information received through the transmission/reception means 3A so that the operator performs the optimum operation, and then allows the transmission/reception means 3A to transmit the generated integrated information to the operating room 2.

If the secondary support rooms 4 are arranged, the experienced doctor refers to a plurality of secondary support information items transmitted therefrom and the endoscopically-observed image and selects the optimum information item used for support to generate integrated information using the remote control system 6, and then transmits the generated integrated information to the operating room 2.

After that, the integrated information transmitted from the primary support room 3 is received by the transmission/reception means 2B in the operating room 2. The received information is reproduced through the reproduction means 2A. The operator performing the operation can recognize the optimum manipulation or description as an image or a voice at the optimum timing. Thus, the remote operation support can be rapidly performed with reliability.

The connection pattern between the endoscopic system 5 in the operating room 2, the remote control system 6 in the primary support room 3, and the remote control system 8 in the secondary support room 4 according to the present invention is not limited to that in the above-mentioned embodiment. For example, according to a modification shown in FIG. 2, the remote control system 6 in the primary support room 3 may be connected to the remote control system 8 in the secondary support room 4 through a two-way communication line. In this instance, transmission/reception means 3A1 capable of realizing two-way communication is provided for the remote control system 6 in the primary support room 3 and transmission/reception means 4B1 similar to the means 3A1 is provided for the remote control system 8 in the secondary support room 4. Accordingly, the secondary support room 4 receives patient information from the operating room 2 and transmits secondary support information to the primary support room 3. Information items are transmitted and received between the primary support room 3 and the secondary support room 4, so that only proper information (integrated information) can be transmitted from the primary support room 3 to the operating room 2. Thus, in the same way as the system shown in FIG. 1, the operating room 2 receives the integrated information from only the primary support room 3 and does not receive examination-result information items which are obtained in the secondary support room 4 and are not selected. Advantageously, the operator in the operating room 2 is free from a troublesome work such as selection of a necessary information item from among information items received.

According to a modification shown in FIG. 3, the endoscopic system 5 in the operating room 2, the remote control system 6 in the primary support room 3, and the remote control system 8 in the secondary support room 4 can be connected to each other through two-way communication lines. Information regarding an operation may be transmitted from the operating room 2 to the primary support room 3 and the secondary support room 4. On the basis of the content of the received information, the primary support room 3 and the secondary support room 4 may transmit proper information items to the operating room 2, respectively. In this case, in addition to the components of the modification shown in FIG. 2, the endoscopic system 5 in the operating room 2 includes transmission/reception means 2B1 capable of realizing two-way communication between the endoscopic system 5 and the remote control systems 6 and 8. Thus, in addition to the advantage of the modification shown in FIG. 2, each of the primary support room 3 and the secondary support room 4 can provide support to the operating room 2 with two-way communication. Thus, wrong support can be prevented.

An support method according to the remote operation support system with the above-mentioned structure will now be described hereinbelow with reference to a flowchart of FIG. 7.

It is assumed that support is given to an operator performing an operation using the remote operation support system shown in FIG. 1. In this case, in a process of step S1 in FIG. 7, an endoscopically-observed image of a body cavity of a patient is obtained using the endoscopic system 5 in the operating room 2. In a process of step S2, the endoscopically-observed image is transmitted from the operating room 2 to the primary support room 3 by the transmission/reception means 2B through the communication line 7.

In a process of step S3, patient information obtained during the operation through the endoscopic system 5 in the operating room 2, or patient information obtained before the operation is transmitted from the operating room 2 to the secondary support room 4 by the transmission/reception means 2B through the communication line 9. The endoscopic system conducts the above-mentioned processes in steps S1 to S3.

In a process of step S4, in the secondary support room 4, the patient information is received from the operating room 2 through the transmission/reception means 4B. A pathologic examination based on the patient information or a pathologic examination of removed tissue is performed using the examination means 4A. The result of the examination, namely, secondary support information is generated through the remote control system 8. In step S5, the secondary support information is transmitted to the primary support room 3 by the transmission/reception means 4B through the communication line 10. The remote control system 8 executes the above processes in steps S4 and S5.

In a process of step S6, in the primary support room 3, the secondary support information transmitted from the secondary support room 4 is received through the transmission/reception means 3A. In a process of step S7, on the basis of the endoscopically-observed image and the secondary support information received in real time, integrated information as the optimum primary support information to be given to the operator is generated through the integration means 3B. In a process of step S8, the integrated information is transmitted to the operating room 2 by the transmission/reception means 3A via the communication line 7. The remote control system 6 executes the above processes in steps S6 to S8.

In this case, if the secondary support rooms 4 are arranged and a plurality of secondary support information items are transmitted therefrom to the primary support room 3, a supporter selects at least one secondary support information item necessary for the optimum support to generate integrated information on the basis of the selected secondary support information item through the integration means 3B.

In a process of step S9, in the operating room 2, the integrated information transmitted from the primary support room 3 is received by the transmission/reception means 2B. In a process of step S10, the received integrated information is reproduced by the reproduction means 2A, thus generating the integrated information as a voice or an image. Thus, the optimum information for operation support can be provided to the operator during the operation so that he or she can recognize the information. Advantageously, the operator does not receive examination-result information items which are obtained in the secondary support rooms 4 and are not selected. The operator can be supported so as to rapidly perform the operation with reliability without receiving a burden of selection of the necessary information item from among the received information items.

The concrete electrical circuit configuration of the remote operation support system according to the present embodiment will now be described in detail with reference to FIGS. 4 to 6, the circuit configuration capable of embodying the foregoing remote operation support method.

Referring to FIG. 4, the remote operation support system 1 according to the present invention comprises the endoscopic system 5 disposed in the operating room 2, the remote control system 6 disposed in a control room as the primary support room 3 in a remote location, and the remote control system 8 disposed in a control room as the secondary support room 4. The endoscopic system 5 is connected to the remote control system 6 via the telecommunication line 7 such as an Integrated Services Digital Network (ISDN) or a LAN. The endoscopic system 5 is connected to the remote control system 8 via the public line 9 serving as a communication line.

The remote control system 6 in the primary support room 3 is similarly connected to the remote control system 8 in the secondary support room 4 via the public line 10.

The endoscopic system 5, arranged in the operating room 2, includes the above-mentioned reproduction means 2A and transmission/reception means 2B. Specifically, the endoscopic system 5 has an endoscope 11 serving as an imaging device for observing a portion to be treated in a body cavity of a patient, peripheral equipment 12 serving as operation equipment such as an electrocautery (not shown) for treatment, a gas insufflator, and an ultrasonic surgical instrument. The peripheral equipment 12 is powered by a drive power supply via a cord or the like. An output value of the peripheral equipment 12 can be variably set.

The endoscope 11 has, for example, a rigid insertion portion. A detachable television camera 14 functioning as endoscopic imaging means is attached to an eyepiece arranged at the proximal end of the insertion portion. The television camera 14 includes: an imaging optical system comprising a plurality of optical lenses; and an imaging element such as a charge-coupled device (hereinbelow, referred to as a CCD) 13.

A light guide cable (not shown) extending from the endoscope 11 is connected to a light source (not shown). An illumination beam of a lamp arranged in the light source is transmitted to the distal end of the insertion portion through the light guide cable and a light guide in the endoscope 11, thus illuminating a body cavity through an illumination window.

An objective lens is attached to an observation window adjacent to the illumination window. An optical image of a subject is formed at the front end of a relay lens system serving as optical-image transmission means arranged in the insertion portion and the formed image is transmitted to the rear end of the relay lens system, so that the optical image magnified is observed through the eyepiece.

The optical image transmitted through the relay lens system is formed on the CCD 13 of the television camera 14 attached to the eyepiece. The CCD 13 photoelectrically converts the image into image signals. The image signals are transmitted to a camera control unit (hereinbelow, referred to as a CCU) 16 functioning as an image processing device through a signal cable 15. The CCU 16 generates standard video signals on the basis of the image signals.

The video signals generated through the CCU 16 are output to a first display (hereinbelow, referred to as a monitor) 17 serving as a main component of the reproduction means 2A. Thus, the endoscopic image captured by the endoscope 11 is displayed on a monitor screen.

The television camera 14 is connected to a visual-field change unit 18 serving as a visual-field control unit for moving at least one of the imaging optical system and the CCD 13 to change the imaging area or the viewing direction. The visual-field change unit 18, the CCU 16, and the peripheral equipment 12 are connected to a system controller 19 functioning as a control unit for controlling those components.

A touch panel 20 used in entering instructions for various controls and a magnetic card reader 21 for input of patient data are connected to the system controller 19. The operator operates the touch panel 20, thus allowing the system controller 19 to change a color tone controlled through the CCU 16 and the imaging distance between the imaging optical system and the CCD 13, and further control an output of the peripheral equipment 12.

Specifically, for example, when an electrocautery is used as the peripheral equipment 12, an output level for cutting or coagulation can be set or controlled. When a gas insufflator is used, a set pressure can be changed or controlled. Patient data recorded in a magnetic card is read by the magnetic card reader 21, the patient data is supplied to the system controller 19, and the data is then output from the system controller 19 to the CCU 16, so that the patient data can be superimposed on an endoscopic image.

The CCU 16 is connected to operating-room signal transmission devices 22 and 23 serving as the transmission/reception means 2B.

When the system according to the present invention is arranged in the foregoing connection pattern shown in FIG. 3, the system controller 19 is connected to the operating-room signal transmission devices 22 and 23 through switch means 24 which can be controlled through the system controller 19. In this case, the switch means 24 can selectively receive integrated information transmitted from the primary support room 3 or secondary support information transmitted from the secondary support room 4 and then transmit the received information to the operating room 2.

According to the present embodiment, the operating-room signal transmission devices 22 and 23, serving as the transmission/reception means 2B, convert video signals of an endoscopic image generated through the CCU 16 and control signals or patient data controlled through the system controller 19 into signals which can be transmitted through the telecommunication lines 7 and 9 and then generate the signals to the primary support room 3 and the secondary support room 4, respectively.

In this instance, the operating-room signal transmission device 22 converts signals, which are obtained by conversion through a control-room signal transmission device 25 in the primary support room 3 and are supplied via the telecommunication line 7, into original video signals and instruction signals and then generates the converted signals as instruction signals to the system controller 19. The control-room signal transmission device 25, which will be described later, corresponds to the transmission/reception means 3A. The original video signals and the instruction signals will be described later. Further, the operating-room signal transmission device 22 generates the video signals to an auxiliary monitor 27, which is connected thereto, to display image information transmitted from the primary support room 3 on a monitor screen.

When the system according to the present invention is arranged in the foregoing connection pattern shown in FIG. 3, the operating-room signal transmission device 23 similarly converts signals, which are obtained by conversion through a control-room signal transmission device 26 in the secondary support room 4 and are supplied via the public line 9, into original video signals and instruction signals and then generates the converted signals as instruction signals to the system controller 19. The control-room signal transmission device 26, which will be described later, corresponds to the transmission/reception means 4B. The original video signals and the instruction signals will be described later. Further, the operating-room signal transmission device 23 generates the video signals to the auxiliary monitor 27, which is connected thereto, to display image information transmitted from the secondary support room 4 on the monitor screen.

Moreover, a keyboard (not shown) serving as input means used by the operator is connected to the system controller 19. Thus, a comment can be input with the keyboard and the comment can be transmitted from the system controller 19 to the supporters in the primary and secondary support rooms 3 and 4 through the operating-room signal transmission devices 22 and 23, and the telecommunication line 7 and the public line 9, respectively.

On the other hand, the remote control system 6 in the primary support room 3 mainly comprises the transmission/reception means 3A and the integration means 3B. Specifically, the remote control system 6 is connected to the telecommunication lines 7 and 10. The remote control system 6 includes the control-room signal transmission device 25 serving as the transmission/reception means 3A. Moreover, the remote control system 6 further includes a monitor 28, a remote controller 30, and an indoor camera 32. The monitor 28 is connected to the control-room signal transmission device 25 and is one of monitors displaying a video signal output from the control-room signal transmission device 26. The remote controller 30 serves as the integration means 3B. The indoor camera 32, connected to the control-room signal transmission device 25, images a chart in the control room or the facial expression of the supporter. The control-room signal transmission device 25 converts signals, supplied from the operating-room signal transmission device 22 via the telecommunication line 7, into video signals generated by the CCU 16 and control signals or patient data controlled through the system controller 19. The control-room signal transmission device 25 similarly converts integrated information generated by the integration means 3B into signals and then outputs the converted signals to the operating-room signal transmission device 22 via the telecommunication line 7. The remote controller 30, connected to the control-room signal transmission device 25, receives the control signals or the patient data sent from the control-room signal transmission device 25. The remote controller 30 serves as control means having a program of calculating a distance by which a visual field (field of view) is shifted. The distance will be described later.

The remote control system 8 in the secondary support room 4 mainly comprises the examination means 4A and the transmission/reception means 4B. The remote control system 8 is connected to the public lines 9 and 10. The remote control system 8 includes the control-room signal transmission device 26 serving as the transmission/reception means 4B. The remote control system 8 further includes a monitor 29, a remote controller 31, and an indoor camera 33. The monitor 29 is connected to the control-room signal transmission device 26 and is one of monitors displaying video signals output from the control-room signal transmission device 26. The remote controller 31 functions as the examination means 4A. The indoor camera 33, connected to the control-room signal transmission device 26, images a chart in the control room or the facial expression of the supporter. The control-room signal transmission device 26 converts signals, supplied from the operating-room signal transmission device 23 via the public line 9, into video signals generated by the CCU 16 and control signals or patient data controlled through the system controller 19. The control-room signal transmission device 26 similarly converts examination-result information generated through the examination means 4A into signals and then outputs the converted signals to the control-room signal transmission device 25. The remote controller 31, connected to the control-room signal transmission device 26, receives the control signals or the patient data output therefrom. The remote controller 31 also functions as control means having a program of calculating a distance by which a visual field is shifted or a program of making an examination on the basis of the patient data. The distance will be described later.

A display 34 is connected to the remote controller 30 and a display 35 is connected to the remote controller 31. Each of the displays 34 and 35 serves as display means for capturing an endoscopic image sent from the CCU 16 as a still image and superimposing patient information sent from the system controller 19 on the endoscopic image. A touch panel or a keyboard 36 is connected to the remote controller 30. A touch panel or a keyboard 37 is connected to the remote controller 31. Each touch panel or keyboard functions as input means used in entering the content of control.

Therefore, in the secondary support room 4, the remote control system 8 receives patient information obtained in the operating room 2 through the control-room signal transmission device 26, analyzes the patient information using the remote controller 31, and outputs an examination result, serving as the analysis result, as secondary support information to the control-room signal transmission device 26.

On the other hand, in the primary support room 3, the remote control system 6 receives the secondary support information obtained in the secondary support room 4 through the control-room signal transmission device 25, generates integrated information using the remote controller 30 on the basis of the received secondary support information and a video signal supplied from the operating room 2, and outputs the generated integrated information as primary support information to the operating-room signal transmission device 22 in the operating room 2.

Referring to FIG. 5, in the operating room 2, the system controller 19 mainly comprises a central processing unit (hereinbelow, referred to as a CPU) 38, a hard disk drive (hereinbelow, referred to as an HDD) 39, a memory 40, an input/output interface (hereinbelow, referred to as an I/O) 41, a video capture control unit 42, and a keyboard interface (hereinbelow, referred to as a keyboard I/F) 43, those components being connected to each other through a bus. The CPU 38 performs the control operation. In the HDD 39, an operating program of the CPU 38 and images are stored. The memory 40 is used to temporarily store images and is also used as a work area. The I/O 41 facilitates input and output through the operating-room signal transmission devices 22 and 23. The video capture control unit 42 captures a video signal and superimposes data on an image. The keyboard I/F 43 is connected to, for example, the keyboard.

Communication of control signals with the operating-room signal transmission devices 22 and 23 is performed through the I/O 41. The operating program of the system controller 19 is stored in the HDD 39.

Accordingly, in the primary support room 3, when setting is performed through the remote controller 30, serving as a control unit, using the keyboard 36 in order to control the operation of the peripheral equipment 12, the content of control is transmitted through the control-room signal transmission device 25, the telecommunication line 7, and the operating-room signal transmission device 22 and is then stored in the memory 40 in the system controller 19 through the I/O 41.

In the case where the operating room 2 is connected to the secondary support room 4 through the communication line capable of realizing two-way communication as shown in FIG. 3, when setting is performed through the remote controller 31, functioning as a control unit, using the keyboard 37 in the secondary support room 4 in order to control the operation of the peripheral equipment 12, the content of control is transmitted through the control-room signal transmission device 26, the public line 9, and the operating-room signal transmission device 23 and is then stored in the memory 40 in the system controller 19 through the I/O 41.

The input means such as the keyboard 36 or 37 is used to enter primary support information such as a direction or advice regarding the operation for, for example, the operator in the operating room 2. The primary support information, namely, integrated information is transmitted through the control-room signal transmission device 25 and the telecommunication line 7 so that the integrated information as the primary support information is superimposed, namely, overlaid on a screen display area 49 of a display area 48 as shown in FIG. 6. Thus, the integrated information is displayed on the screen of the auxiliary monitor 27 in the operating room.

Consequently, the operator in the operating room can rapidly perform the operation with reliability on the basis of the integrated information as the optimum primary support information on the auxiliary monitor 27. The integrated information is transmitted from the primary support room 3 as the control room in a remote location.

Referring to FIG. 6, the display area 48 includes the display segment 49 where an endoscopic image transmitted from the operating room 2 is displayed, a display segment 50 where reference images such as tomograms are displayed, a display segment 51 where various set values of the peripheral equipment 12 are displayed, a display segment 52 where personal information of a patient is displayed, and a display segment 53 where various comments may be displayed.

Directions may be given to the operator in the operating room 2 using images. If the foregoing program of calculating a distance by which the visual field is shifted is installed in the remote controller 30 or 31, the calculated distance is supplied from the remote controller 30 or 31 to the system controller 19. In this instance, positional information entered using the input means such as the keyboard 36 or 37 is stored in a memory (not shown) in the remote controller 30 or 31. On the basis of the stored positional information, the distance is calculated. On the basis of the calculated distance, the remote controller 30 or 31 generates an instruction signal to the visual-field change unit 18. Information as the instruction signal generated is supplied from the remote controller 30 or 31 to the system controller 19. Alternatively, information such as the distance may be supplied from the remote controller 30 or 31 to the system controller 19 and the system controller 19 may generate an instruction signal on the basis of the distance.

If the program of calculating a distance by which the visual field is shifted is installed in the HDD 39 of the system controller 19, positional information of a cursor is supplied from the remote controller 30 or 31 to the system controller 19 and is then stored in the memory 40 through the I/O 41. In this case, the supporter clicks at a point A at which a cursor 54 is located in the screen display area 49 on the monitor shown in FIG. 6, and then moves the cursor 54 to a point B via dragging, so that positional information items of the points A and B are stored in the memory 40 of the system controller 19. According to the program stored in the HDD 39, on the basis of the positional information items, a distance by which the visual field is shifted is calculated from at least one of a moving distance between the points A and B as displacement, a moving direction as a displacement angle, and a moving speed as a displacement rate. On the basis of the calculated distance, an instruction signal for the visual-field change unit 18 is generated.

The generated instruction signal is supplied to the visual-field change unit 18. For instance, when receiving the instruction signal from the remote controller 30 or 31, the system controller 19 allows the visual-field change unit 18 to change a distance between the imaging optical system and the CCD 13 in accordance with the calculation result. Thus, the endoscopic image is displayed such that a portion corresponding to the point A is shifted to the point B in the screen display area 49.

In other words, the supporter observes an endoscopic image displayed on the monitor screen of the monitor 28 or 29. When the displayed endoscopic image does not include a desired imaging area or the image is not based on a desired viewing direction, the supporter superimposes, namely, overlays the endoscopic image, which is displayed on the monitor 28 or 29, on the screen display area 49 of the display 34 or 35. After that, he or she enters an instruction using the input means such as the keyboard 36 or 37 in order to control the visual-field change unit 18 to change the imaging area or viewing direction.

Information of the instruction entered through the input means is transmitted as an instruction signal from the remote controller 30 or 31 to the system controller 19 in the operating room through the control-room signal transmission device 25 or 26 and the telecommunication line 7 or 9. On the basis of the instruction signal, the system controller 19 outputs a control signal to the visual-field change unit 18 to change the imaging distance between the imaging optical system and the CCD 13.

In response to the control signal, the visual-field change unit 18 moves at least one of the imaging optical system and the CCD 13 to change the imaging distance. Thus, the desired endoscopic image obtained on the basis of the instruction of the supporter in the support room can be displayed on the monitor screen of the monitor 17, that of the monitor 28 or 29, and the display area of the display 34 or 35.

The above embodiment has been described on the assumption that the operating room 2 is connected to the secondary support room 4 through the communication line capable of one-way communication through which patient information is transmitted from the operating room 2 to the secondary support room 4, the secondary support room 4 is connected to the primary support room 3 through the communication line capable of one-way communication through which secondary support information is transmitted from the secondary support room 4 to the primary support room 3, and the operating room 2 is connected to the primary support room 3 through the communication line capable of two-way communication through which patient information such as an endoscopically-observed image and integrated information (primary support information) can be transmitted therebetween. Referring to FIG. 3, in the case where the respective rooms are connected to each other so that the supporters in the primary and secondary support rooms 3 and 4 transmit support information items in parallel with each other to the operating room 2, as mentioned at the beginning, information items may be concentrated on the operating room 2, resulting in operation delay. In this case, the switch means 24 is controlled using the touch panel 20 so that information is transmitted from the secondary support room 4 to the primary support room 3. Thus, the above disadvantage can be overcome.

According to the above-mentioned embodiment, therefore, patient information is transmitted from the operating room 2 to the secondary support room 4 during or before the operation, an examination is made on the basis of the patient information in the secondary support room 4, and the result of the examination is then transmitted as secondary support information to the primary support room 3. In the primary support room 3, integrated information is generated on the basis of an endoscopically-observed image in the operation and the secondary support information. The integrated information is transmitted to the operating room 2. The transmitted integrated information is reproduced by the reproduction means in the operating room 2. Thus, the optimum operation support can be rapidly given to the operator with reliability. When the operation includes transplantation or a pathologic examination, patient information can be transmitted to the secondary support room without moving removed tissue or a specimen thereto. Thus, immediate determination can be achieved. The optimum support can be similarly provided.

The supporter in a remote location can observe endoscopic images, obtained in the operation in the operating room, in the monitor and the display and also obtain patient information. Moreover, the supporter controls the endoscopic image in the display using the input mean, so that he or she can remotely control the visual-field change unit in the operating room through the communication line, thus displaying a desired endoscopic image on the monitor screen. Consequently, the supporter can understand the operating condition in substantially real time and rapidly provide support information for the proper operation to the operator in the operating room from a distance. When an exacting operation is performed, the supporter can also rapidly understand the operating condition with accuracy and smoothly provide prompt operation support.

In the above description, the operating room and the primary and secondary support rooms may be separated from each other in the sense of a remote location. For example, if those rooms are included in the same building, so long as the respective rooms are separated from each other, it may be assumed that the rooms are arranged at remote sites.

The present invention is not limited to the foregoing embodiment and modifications but the combinations of the embodiment and the modifications and many variations are possible.

What is claimed is:

1. A remote operation support system comprising:
a first control system disposed in an operating room;
a second control system disposed in a primary support room; and
a third control system disposed in at least one secondary support room, the first to third control systems being connected to each other through communication lines, wherein
the first control system comprises:
an imaging device for imaging a portion to be treated of a patient under operation to obtain an image signal;

a first transmission/reception device for transmitting the image signal supplied from the imaging device to the second control system, transmitting patient information regarding the patient under operation to the third control system, and receiving support information from the second control system; and a reproduction device for displaying the image signal and reproducing the support information, the third control system comprises:

a patient-information processing device for processing the patient information transmitted from the first control system to obtain the result of the processing; and a second transmission/reception device for receiving the patient information from the first transmission/reception device of the first control system and transmitting information indicating the processing result, obtained by the patient-information processing device, as secondary support information to the second control system, and the second control system comprises:

an integration device for generating primary support information, used to support an operator in the operating room upon operating, on the basis of the secondary support information transmitted from the third control system and the image signal transmitted from the first control system; and a third transmission/reception device for receiving the image signal sent from the first control system and the secondary support information sent from the third control system, and transmitting the primary support information generated through the integration device to the first control system.

2. The system according to claim 1, wherein the first and second control systems and the second and third control systems are connected to each other through the respective communication lines capable of realizing two-way communication, and the first and third control systems are connected to each other through the communication line capable of realizing one-way communication from the first control system to the third control system.

3. The system according to claim 1, wherein the first and second control systems, the first and third control systems, and the second and third control systems are connected to each other through the respective communication lines capable of realizing two-way communication.

4. The system according to claim 3, wherein the first transmission/reception device of the first control system is connected to the second and third transmission/reception devices through a switch for switching between the second and third control systems.

5. The system according to claim 1, wherein when there are a plurality of third control systems, the integration device of the second control system generates the integrated information on the basis of a plurality of secondary support information items obtained through the respective third control systems and the image signal sent from the first control system, and transmits the generated information to the first control system.

6. The system according to claim 1, wherein the imaging device includes an endoscopic imaging device having an imaging optical system and an imaging element to image a body cavity, and the first control system further comprises:

an image processing unit for converting the image signal, obtained by photoelectric conversion through the imaging element of the endoscopic imaging device, into a video signal; and a first display for displaying an endoscopic image based on the video signal converted and generated through the image processing unit.

7. The system according to claim 6, wherein the first control system further comprises:

a visual-field control unit for controlling an imaging area or the viewing direction of the endoscopic imaging device; and a first control unit for controlling at least the visual-field control unit, at least one of the second and third control systems further includes:

a second control unit for generating an instruction signal to control the visual-field control unit to the first control unit, and the instruction signal generated through the second control unit is transmitted to the first control unit to control the imaging area or the viewing direction of the endoscopic imaging device.

8. The system according to claim 1, wherein the first and third control systems are connected to each other through the communication line capable of realizing one-way communication through the first control system to the third control system.

9. A remote operation support method using a system including a first control system disposed in an operating room, a second control system disposed in a primary support room, and a third control system disposed in at least one secondary support room, the first to third control systems being connected to each other through communication lines, the method comprising:

a patient-information obtaining step of obtaining patient information through the first control system;

a first transmitting step of transmitting, by the first control system, the patient information obtained in the patient-information obtaining step to the third control system;

a first receiving step of receiving, by the third control system, the patient information transmitted in the first transmitting step;

a second transmitting step of transmitting secondary support information based on the patient information from the third control system to the second control system;

a second receiving step of receiving, by the second control system, the secondary support information transmitted in the second transmitting step;

a third transmitting step of transmitting primary support information based on the secondary support information from the second control system to the first control system;

a third receiving step of receiving, by the first control system, the primary support information transmitted in the third transmitting step; and a reproducing step of reproducing, by the first control system, the primary support information received in the third receiving step as an image or a voice.

10. The method according to claim 9, wherein the first and second control systems and the second and third control systems are connected to each other through the respective communication lines capable of realizing two-way communication, and the first and third control systems are connected to each other through the communication line capable of realizing one-way communication from the first control system to the third control system.

11. The method according to claim 9, wherein the first and second control systems, the first and third control systems, and the second and third control systems are connected to each other through the respective communication lines capable of realizing two-way communication.

12. The method according to claim 11, wherein a first transmission/reception device of the first control system is connected to second and third transmission/reception devices through a switch for switching between the second and third control systems.

13. The system according to claim 9, wherein when there are a plurality of third control systems, an integration device of the second control system generates integrated information on the basis of a plurality of secondary support information items obtained through the respective third control systems and an image signal sent from the first control system, and transmits the generated information to the first control system.

14. The method according to claim 9, wherein
the first control system comprises:
an endoscopic imaging device having an imaging optical system and an imaging element to image a body cavity;
an image processing unit for converting an image signal, obtained by photoelectric conversion through the imaging element of the endoscopic imaging device, into a video signal; and
a first display for displaying an endoscopic image based on the video signal converted and generated through the image processing unit.

15. The method according to claim 14, wherein
the first control system further comprises:
a visual-field control unit for controlling an imaging area or the viewing direction of the endoscopic imaging device; and
a first control unit for controlling at least the visual-field control unit, and
the method further includes:
a step of controlling the imaging area or the viewing direction of the endoscopic imaging device on the basis of an instruction signal to control the visual-field control unit, the instruction signal being transmitted from at least one of the second and third control systems.

16. A remote operation support method using a system including a first control system disposed in an operating room, a second control system disposed in a primary support room, and a third control system disposed in at least one secondary support room, the first to third control systems being connected to each other through communication lines, the method comprising:
an imaging step of imaging a portion to be treated of a patient under operation in the operating room to obtain an image signal;
a first transmitting step of transmitting the image signal obtained in the imaging step from the first control system to the second control system;
a second transmitting step of transmitting patient information regarding the patient under operation from the first control system to the third control system;
a first receiving step of receiving, by the first control system, support information from the second control system;
a reproducing step of displaying, by the first control system, the image signal and reproducing, thereby, the support information to support an operator;
a second receiving step of receiving, by the third control system, the patient information transmitted from the first control system;
a patient-information processing step of processing, by the third control system, the patient information transmitted from the first control system to obtain the result of the processing;
a third transmitting step of transmitting the processing result, obtained in the patient-information processing step, as secondary support information from the third control system to the second control system;
a third receiving step of receiving, by the second control system, the image signal sent from the first control system and the secondary support information sent from the third control system;
an integrating step of generating, by the second control system, primary support information, used to support the operator in the operating room upon operating, on the basis of the secondary support information sent from the third control system and the image signal sent from the first control system; and
a fourth transmitting step of transmitting the primary support information, generated in the integrating step, from the second control system to the first control system.

17. The method according to claim 16, wherein the first and second control systems and the second and third control systems are connected to each other through the respective communication lines capable of realizing two-way communication, and the first and third control systems are connected to each other through the communication line capable of realizing one-way communication from the first control system to the third control system.

18. The method according to claim 16, wherein the first and second control systems, the first and third control systems, and the second and third control systems are connected to each other through the respective communication lines capable of realizing two-way communication.

19. The method according to claim 16, wherein when there are a plurality of third control systems, an integration device of the second control system generates integrated information on the basis of a plurality of secondary support information items obtained through the respective third control systems and an image signal sent from the first control system, and transmits the generated information to the first control system.

20. The method according to claim 16, wherein
the first control system comprises:
an endoscopic imaging device having an imaging optical system and an imaging element to image a body cavity;
an image processing unit for converting an image signal, obtained by photoelectric conversion through the imaging element of the endoscopic imaging device, into a video signal; and
a first display for displaying an endoscopic image based on the video signal converted and generated through the image processing unit.

21. The method according to claim 20, wherein
the first control system further comprises:
a visual-field control unit for controlling an imaging area or the viewing direction of the endoscopic imaging device; and
a first control unit for controlling at least the visual-field control unit, and
the method further includes:
a step of controlling the imaging area or the viewing direction of the endoscopic imaging device on the basis of an instruction signal to control the visual-field control unit, the instruction signal being transmitted from at least one of the second and third control systems.

* * * * *